(12) United States Patent
Pettit

(10) Patent No.: US 6,548,644 B1
(45) Date of Patent: Apr. 15, 2003

(54) SITE PROTECTED PROTEIN MODIFICATION

(75) Inventor: Dean K. Pettit, Seattle, WA (US)

(73) Assignee: Immunex Corporation, Seattle, WA (US)

( * ) Notice: Subject to any disclaimer, the term of this patent is extended or adjusted under 35 U.S.C. 154(b) by 0 days.

(21) Appl. No.: 08/814,305

(22) Filed: Mar. 10, 1997

(51) Int. Cl.$^7$ .................. C07K 14/00; C07K 16/00; A61K 39/395
(52) U.S. Cl. .................. 530/402; 530/334; 530/337; 530/389.2; 530/391.7; 530/409; 530/410; 530/810; 424/143.1; 424/146.1; 424/178.1; 424/182.1
(58) Field of Search .................. 530/402, 334, 530/337, 389.2, 391.7, 409, 410, 810; 424/143.1, 146.1, 178.1, 182.1

(56) References Cited

U.S. PATENT DOCUMENTS

| | | | | |
|---|---|---|---|---|
| 4,179,337 A | * | 12/1979 | Davis et al. | 435/181 |
| 5,235,028 A | * | 8/1993 | Barany et al. | 528/335 |
| 5,514,572 A | * | 5/1996 | Veronese et al. | 435/180 |

FOREIGN PATENT DOCUMENTS

| | | | |
|---|---|---|---|
| WO | WO 94/13322 | * | 6/1994 |
| WO | WO 94/20069 | * | 9/1994 |
| WO | WO 96/11213 | * | 4/1996 |

OTHER PUBLICATIONS

Delgado et al., Critical Reviews in Therapeutic Drug Carrier Systems, 9(3,4), pp. 249–304, 1992.*
Mohler et al., *J. Immunol.,* vol. 151, No. 3, pp. 1548–1561, Aug. 1993.*
Paul, W.F. (ed.), *Fundamental Immunology,* 3$^{rd}$ eddition, pp. 807–812, 1993.*
Ware et al., *Immunology,* vol. 147, p. 4229.*
Goodson et al., *Bio/Technology,* vol. 8, pp. 343–346, Apr. 1990.*
Pettit et al, *The Journal of Biological Chemistry,* vol. 272, No. 4, pp. 2312–2318, Jan. 24.*
Lu et al, *Int. J. Peptide Protein Res,* vol. 43, pp. 127–138, 1994.*
Pettit et al, *Polymer Prepr (Am. Chem. Soc. Div. Polym. Chem),* vol. 38, No. 1, pp. 574–575, Apr. 1997.*

Mohler et al., "Soluble Tumor Necrosis Factor (TNF) Receptors are Effective Therapeutic Agents in Lethal Endotoxemia and Function Simultaneously as Both TNF Carriers and TNF Antagonists", *The Journal of Immunology* 151:548–1561, 1993.
Onozaki et al., "Human Interleukin 1 is a Cytocidal Factor for Several Tumor Cell Lines", *The Journal of Immunology* 135:3962–68, Dec. 1985.
Sartore et al., "Accurate Evaluation Method of the Polymer Content in Monomethoxy (Polyethylene Glycol) Modified Proteins Based on Amino Acid Analysis", *Applied Biochemistry and Biotechnology* 31:213–222, 1991.
Goodson et al., "Site–Directed Pegylation of Recombinant Interleukin–2 at its Glycosylation Site", *Bio/Technology* 8:343–46, Apr. 1990.
Kinstler et al., "Characterization and Stability of N–terminally PEGylated rhG–CSF", *Pharmaceutical Research* 13:996–1002, 1996.
Gombotz et al., "Biodegradable Polymers for Protein and Peptide Drug Delivery", *Bioconjugate Chemistry* 6:332–351, 1995.
Pettit et al., "Structure–Function Studies of Interleukin 15 using Site–specific Mutagenesis, Polyethylene Glycol Conjugation, and Homology Modeling", *The Journal of Biological Chemistry* 272:2312–2318, 1997.
Urrutigoity et al., "Biocatalysis in Organic Solvents with a Polymer–Bound Horseradish Peroxidase", *Biocatalysis* 2:145–149, 1989.
Delgado et al., "The Uses and Properties of PEG–Linked Proteins", *Critical Reviews in Therapeutic Drug Carrier Systems* 9:249–304, 1992.
Paul, W.F. (ed), Fundamental Immunology, 3rd edition, pp. 807–812.*

* cited by examiner

*Primary Examiner*—Christopher S. F. Low
*Assistant Examiner*—Abdel A. Mohamed
(74) *Attorney, Agent, or Firm*—Janis C. Henry

(57) ABSTRACT

Processes for conjugating proteins with polyethylene glycol are disclosed. The disclosed processes provide modified proteins having little or no decrease in their activity and include the steps of protecting one or more sites on the protein, contacting the protected protein with polyethylene glycol under conditions suitable for conjugating the polyethylene glycol to the protein, and deprotecting the protein. This advantageous retention of a desired protein activity is attributed to the availability of one or more protein binding sites which is unaltered in the conjugation process and thus remains sterically free to interact with a binding partner ligand or cognate subsequent to the conjugation process.

13 Claims, 3 Drawing Sheets

SITE PROTECTED PROTEIN MODIFICATION

BACKGROUND OF THE INVENTION

1. Field of the Invention

The present invention relates to processes for modifying proteins. More particularly, the present invention involves processes for linking polyethylene glycol to proteins in a manner which provides advantages associated with polyethylene glycol conjugated proteins while maintaining a desired protein bioactivity.

2. Description of Related Art

Processes and reagents for chemically modifying proteins have been used extensively for decades. Traditionally, protein chemical modifications were carried out in order to study their functional properties and structural characteristics. With the emergence of recombinant DNA techniques and protein therapeutics, researchers have chemically modified proteins to alter their therapeutic properties. In particular, processes for conjugating proteins with polyethylene glycol have gained widespread use within the pharmaceutical and biochemical communities as a result of numerous improved pharmacological and biological properties associated with polyethylene glycol conjugated proteins. For example, polyethylene glycol modification is known to extend significantly the plasma half life of proteins used in clinical applications, thus substantially improving the clinical usefulness of the protein. Polyethylene glycol conjugation also is known to reduce the antigenicity and immunogenicity of proteins, thereby reducing life-threatening anaphylaxis.

Another benefit associated with polyethylene glycol modified proteins is that water solubility which is increased as a result of the high water solubility of polyethylene glycol. The increased water solubility can improve the protein's formulation characteristics at physiological pH's and can decrease complications associated with aggregation of low solubility proteins.

Additionally, polyethylene glycol conjugated proteins have found use in bioindustrial applications such as enzyme based reactions in which the reaction environment is not optimal for the enzyme's activity. For example, some polyethylene glycol conjugated enzymes demonstrate a wider optimum pH activity and reduced optimum activity temperature. Moreover, enzymes having reduced activity in many organic solvents have been successfully conjugated with polyethylene glycol to a degree that renders them useful for catalyzing reactions in organic solvents. For example, polyethylene glycol has been conjugated with horseradish peroxidase which then becomes soluble and active in chloroform and toluene (Urrotigoity et al., *Biocatalysis*, 2:145–149, 1989).

Polyethylene glycol conjugated proteins vary in the extent to which plasma circulation half life is increased, immunogenicity is reduced, water solubility is enhanced, and enzymatic acitivity is improved. Factors responsible for these variations are numerous and include the degree to which the protein is substituted with polyethylene glycol, the chemistries used to attach the polyethylene glycol to the protein, and the locations of the polyethylene glycol sites on the protein.

The most common methods for attaching polyethylene glycol to proteins involve activating at least one of the hydroxyl groups on the polyethylene glycol with a functionality susceptible to nucleophilic attack by the nitrogen of amino groups on the protein. These methods generally result in loss of biological activity due to the nonspecific attachment of polyethylene glycol Alternative approaches to conjugating proteins with polyethylene glycol include controlling the conjugation reactants and conditions so that the conjugation site is confined to the N-terminus (Kinstler et al. *Pharm. Res.* 13:996, 1996) attaching polyethylene glycol to protein carbohydrate functionalities (Urrutigoity, et al. *Biocatalysis* 2:145, 1989) and attaching polyethylene glycol at protein cysteine residues (Goodson et al. *Biotechnology* 8:343, 1990). While these offer some degree of control of the reaction site, there is a continuing need for improved methods for providing polyethylene glycol conjugated proteins. In particular, it would be desirable to provide methods for conjugating proteins with polyethylene glycol that result in modified proteins having enhanced bioactivity or little loss in bioactivity while maintaining the benefits of polyethylene glycol conjugation, including substantially decreased immunogenicity, increased solubility, and prolonged circulation half lives characteristic of modified proteins.

SUMMARY OF THE INVENTION

The present invention provides protein modification processes that result in modified proteins having little or no decrease in an activity associated with the protein. More particularly, the invention described herein includes processes for modifying a protein by first protecting a site on the protein and then contacting the protected protein with polyethylene glycol under conditions suitable for linking the polyethylene glycol to the protein. After deprotecting the protein, the resulting polyethylene glycol modified protein has improved characteristics over proteins modified according to prior art procedures. An advantageous retention of activity is attributed to the availability of one or more protein binding sites which is unaltered in the conjugation process and thus remains sterically free to interact with a binding partner subsequent to the conjugation process.

DETAILED DESCRIPTION OF THE INVENTION

Figure 1:
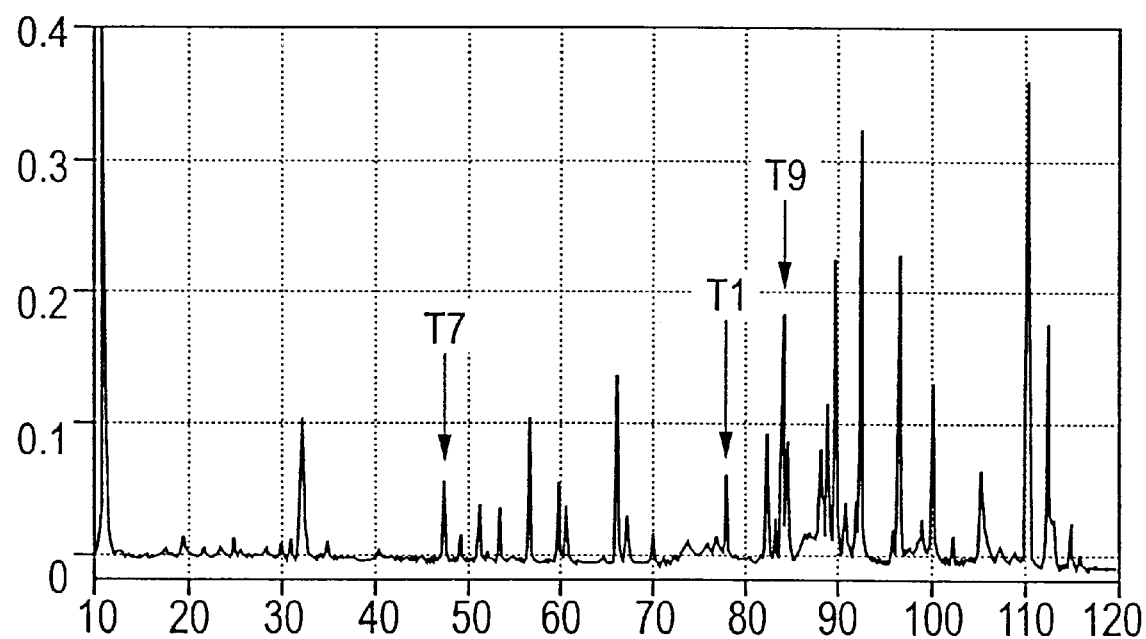
FIG. 1 is a p75 TNFR:Fc peptide map obtained by the reverse phase HPLC separation of TNFR:Fc trypsin digestion fragments.

The present invention provides processes and reagents for conjugating proteins or polypeptides with polyethylene glycol in a manner that results in polyethylene glycol conjugated proteins having little or no reduction in a desired activity. More specifically, the present invention provides processes for conjugating polyethylene glycol with proteins under conditions which preclude polyethylene glycol conjugation at sites on the protein. Advantageously, because the sites are not subject to conjugation with polyethylene glycol, a protein conjugated according to the present invention maintains a desired activity while demonstrating benefits associated with polyethylene glycol conjugation. The processes are based upon the discovery that by protecting one or more cognate sites, substrate binding sites or other binding sites on a protein, conjugating the protected protein with polyethylene glycol, and subsequently deprotecting the protein, the resulting polyethylene modified protein does not demonstrate a reduction in a desired activity.

Any protein is suitable for polyethylene glycol modification in accordance with the present invention including but not limited to protein ligands, receptors, antigens, antibodies, enzymes, protein fragments, peptides, and polypeptides. Particularly desirable protein candidates for polyethylene glycol modification as described herein ale those which, subsequent to their modification by prior art methods, demonstrate a reduction in a desired activity. Other proteins which are suitable for modification in accordance with the present invention are those having multiple binding sites. In this embodiment, a protein may be conjugated so that an activity associated with one or more of the multiple binding sites can be reduced while maintaining an activity associated with one or more different binding sites. This is accomplished by protecting only selected binding sites and leaving other binding sites unprotected and available for polyethylene glycol conjugation. The resulting polyethylene glycol conjugated protein will have an activity associated with the protected binding sites and, depending upon the degree to which unprotected sites are involved in the conjugation process, will have a diminished, or no activity, associated with unprotected sites. This approach is useful in cases in which cognate or substrate binding to one or more protein binding sites is desirably suppressed in certain clinical, diagnostic or industrial applications.

Proteins that may be modified in accordance with the present invention include those having utility in clinical and diagnostics applications and those used in the biotechnology industry, such as enzymes in bioreactors. Receptors which may be modified as taught herein include cytokine receptors, for example, TNFR, IL-4R, IL-1R, IL-17R, IL-15R, p55 TNFR:Fc and p75 TNFR:Fc. Candidate antibodies for conjugation include but are not limited to OKT3 (anti-T-Cell), CENTNF™ (anti-TNF) and anti Her2/Neu. Enzymes of interest for conjugation include CD39, tPA, and DNAse™ an enzyme marketed by Genentech for the treatment of MS. Many proteins have multimeric binding sites and require more than one association for activity. Such proteins are particularly desirable for modification since loss of one binding site leaves the whole protein inactive. Members of the group of multimeric proteins include TNF, hGH, CD40L, and FasL. Other candidate protein ligands are known to bind multiple receptor subunits and include IL-2, IL-15, GM-CSF, and G-CSF.

In accordance with the present invention protecting a site on the protein can be accomplished with a variety of suitable protecting agents and procedures for forming complexes of the protecting agent and protein. In the context of the present invention, protecting agents include any molecule having the capability of reversibly binding or associating with a site on a protein which may be one or more amino acids. When the site includes more than one amino acid, the amino acids may be contiguous, or the protein's conformation may place the amino acids in close spatial proximity. Sites include, but are not limited to cognate sites or substrate binding sites which are associated with a protein activity. For example, a protecting agent in the form of an antibody immunoreactive against a protein selected for polyethylene glycol conjugation can be bound to a selected active site on the protein using binding methodologies known in the art. Preferably, a selected antibody binding agent is raised against a site of the selected protein that confers the activity of interest or the site having the activity targeted for preservation. Conversely, an antigen can be a protecting agent for an antibody selected for modification in accordance with the present invention by acting to protect selected sites on the antibody and then conjugating the antibody with polyethylene glycol. Methods for producing antibodies and methods for providing protein-antibody complexes are known in the art and within the knowledge of those skilled in the art.

Alternative approaches for protecting the cognate site, substrate site, or binding site include utilizing a receptor or ligand as a protecting agent on the cognate protein selected for modification. Such receptor or ligand protecting agents need not be the natural cognate or substrate for that protein but need only be capable of sufficient binding affinity for the selected active site or sites on the protein of interest to protect the active site or sites from participating in a polyethylene glycol conjugation reaction. In addition, enzymes having binding sites for a substrate selected for polyethylene glycol modification in accordance with the present invention are suitable protecting agents for the substrate.

In choosing a protecting agent for any selected protein it is desirable to consider certain criteria. One consideration is the relative molecular size of the protecting agent and the protein selected for conjugation. The protecting step yields can be limited by the ratio of the size of the protecting agent to that of the protein selected for conjugation. Typically, the protecting reaction will result in the highest yields when the ratio is near one. In general, the molecular mass of the protecting agent and protein is a measure of their molecular size. Thus, for example, bivalent antibodies have a mass of from about 125 to 150 kDa and under optimized reaction conditions 10 mg of antibody will protect about 20 mg of selected protein having a molecular weight of 150 kDa. On the other hand the antibody may protect as little as 2 mg of a protein having a molecular weight of 15 kDa. Thus, when the protecting agent and the selected protein are similar in mass the protecting step yields may be the highest.

Another factor that may be considered in selecting a protecting agent for a protein is the stability of the protecting agent and the stability of the polyethylene glycol conjugated protein in solutions of deprotecting agent used during the deprotecting step of the invention. As discussed in detail below, the step of deprotecting the conjugated protein from the protecting agent may involve exposing the protecting agent and conjugated deprotected protein to extremes of pH, elevated ionic strength solutions, or chaotropic agents. In cases in which the protecting agent is to be re-used in additional protecting reactions, it is preferable that the protecting agent is selected so that deprotecting the conjugated protein does not require extreme reactions conditions which may lead to the irreversible loss of protecting agent activity.

Another consideration in selecting protecting agents may include any potential toxicity associated with the agent or its use. Proteins conjugated in accordance with the present invention and intended for clinical applications should be substantially free of any substances of a toxic nature. Even though known protein purification processes provide highly pure material, it is preferable to avoid protecting agents having any known toxicity.

Another consideration in selecting a protecting agent is the location of potential polyethylene glycol conjugation sites on the selected protein and their respective proximity to binding sites selected for protection. For selected proteins having potential conjugation sites in close proximity to a site selected for protection, it may be desirable to utilize a protecting agent which is sufficiently large to protect an area on the protein that is in close proximity to the site to which it binds. When the protecting agent is capable of "protecting" a sufficiently large spatial area extending outside the selected binding site, polyethylene glycol conjugation is likely to be precluded or substantially reduced, thus preserving a desired activity of the glycol conjugated protein. The preferred spatially protected area on the protein will depend on spatial orientation of conjugation sites within the protein and size of the polyethylene glycol which is discussed below.

The desired activity of a protein conjugated in accordance with the present invention may be influenced by the selection of protecting agents. For example, proteins which bind multiple receptor subunits may be conjugated with polyethylene glycol such that a first receptor subunit binding site is protected prior to the conjugation reaction and a second receptor subunit binding site is not protected. In this embodiment, polyethylene glycol conjugation is prevented or inhibited at the protected site, thus preserving the site for ligand or receptor binding; and polyethylene glycol conjugation is allowed at unprotected sites, thus making the site less accessible for ligand or receptor binding. This embodiment has value in therapeutic or other clinical applications, because binding sites for one receptor subunit may be preserved while binding to another receptor subunit is prevented. This effect can lead to production of specific antagonists or polyethylene glycol conjugated proteins with other unique modified functions.

Similarly, the present invention provides methodologies for preventing multimeric association of proteins. For example, polyethylene glycol can be selectively conjugated onto sites in or around the multimeric association interface, while preserving the binding of the protein for its natural cognate through "site protected" polyethylene glycol conjugation as taught herein, thus preventing receptor multimerization.

Table I identifies a variety of proteins and possible protecting agents that are suitable candidates for use in the processes of the present invention:

TABLE I

Sample Proteins and Possible Protecting Agents

| Receptors | |
|---|---|
| Il-1R | IL-1, IL-1Rα, antibody (Ab) |
| IL-4R | Il-4, Ab |
| IL-17R | IL-17, Ab |
| p55 TNFR:Fc | TNF, LTα, Ab |
| p75 TNFR:Fc | TNF, LTα, Ab |
| IL-15R | IL-15 |
| Antibodies | |
| OKT3 (anti T-Cell) | T-cells, CD3, Ab |
| CENTNF ™ (anti-TNF | TNF, Ab |
| Her2/Neu Ab | Breast Cancer Antigen, Ab |
| Enzymes | |
| CD39 | Substrate Analogue, Inhibitor, or Cofactor; Ab |
| tPA | Substrate Analogue, Inhibitor, or Cofactor; Ab |
| DNAse ™ | Substrate Analogue, Inhibitor, or Cofactor; Ab |
| Ligands - Multimeric | |

TABLE I-continued

Sample Proteins and Possible Protecting Agents

| Association for Activity | |
|---|---|
| TNF | TNF, TNFR, Ab |
| hGH | hGH, hGHR, Ab |
| CD40L | CD40L Ab |
| FasL | FasL, Ab |
| Ligands Binding Multiple Receptor Subunits | |
| IL-2 | IL-2Rα, IL-2Rβ, IL-2Rγ, Ab |
| IL-15 | IL-15Rα, IL-15Rβ, IL-15Rγ, Ab |
| GM-CSF | GM-CSF Receptors, Ab |
| G-CSF | G-CSF Receptors, Ab |

In preferred embodiments of the present invention, the step of protecting the selected protein is accomplished by first immobilizing one or more protecting agents to a solid support and then bringing the protein in contact with the immobilized protecting agent in a manner that results in the protein binding to the immobilized protecting agent. Advantageously, processes of the present invention that include immobilizing the protecting agent to a solid support can be repeated using the same solid support for subsequent protecting reactions and thus have the benefit of re-using protecting agent without the necessity of separating protecting agent from a reaction mixture. Still another advantage associated with this embodiment is that unreacted polyethylene glycol and conjugation reaction by-products and any side products are easily removed from the polyethylene glycol modified protein by washing the column well before deprotecting the protected modified protein and recovering the conjugated protein from the column. Preferably, the chemical and physical properties of the solid support are such that there is a large surface area for reacting the protecting agent and the protein and that it is stable under a range of reaction conditions, including a variety of pH, temperature, and aqueous and nonaqueous solvents. Additionally, the solid support should be selected so that it immobilizes the protecting agent in a manner that provides sufficient amounts of protecting agent having a site which is available for protecting the protein.

One factor affecting the choice of solid support or column material is the final spatial orientation of the immobilized protecting agent. Preferably, immobilized protecting agent is oriented spatially on the solid support such that it is capable of protecting the selected protein in an optimized manner. To achieve this, using additional active compounds which orient the protecting agent in a desired configuration may be useful. For example, a solid support column containing immobilized protein A or protein G will prepare the column for immobilizing antibodies by binding through the Fc domain of the antibody. Antibodies immobilized in this fashion have a spatial orientation which provides for their maximal binding with the protein selected for conjugation. Another approach which utilizes additional compounds involves using spacers or linkers between the column material and the protecting agent to orient the protecting agent and provide for maximum contact area between the blocking agent and the protein selected for conjugation. Linkers or spacers for proteins and biomolecules in general are widely available from commercial sources including Pierce Chemical and Sigma Chemical. Optimum reaction conditions and preferred applications for the spacers or linkers are well known in the art. For example, Wong, *Chemistry of Protein Conjugation and Cross-linking*, CRC Press, 1993 describes using reagents for linking proteins and other molecules to a variety of functional groups through heterobifunctional reagents and homobifunctional reagents Solid supports having good structural and chemical stability in a variety of reaction conditions are commercially available. These supports are typically in the form of beads or particulates, are fabricated of a cross linked polymer and are available with a variety of immobilizing mechanisms. For example, solid supports having the capability of cationically or anionically interacting with compounds having oppositely charged ionic functional groups can be used to bind protecting agents via an ionic moiety. Ionic exchange solid supports are widely available and include functionalities such as charged amino groups, carbonates, acidic and basic groups of varying ionic strength and pH. Similarly, suitable solid supports include those having a specific binding functionality capable of binding to a portion of a protein of interest. For example, solid supports incorporating a ligand for the Fc portion of IgG an be used to immobilize antibodies or Fc fusion proteins. Suitable commercially available columns include those having solid supports with bound protein A and protein G both of which will bind selected portions of IgG. Still other suitable solid supports are those having active reactive sites for covalently attaching desired protecting agent. Solid supports having this characteristic include those incorporating functionalities which react with nucleophiles such as amino groups, hydroxyl groups and sulfhydryl groups. Example 1 below describes the use of one such commercially available solid support, EMPHAZE™(available from Pierce Chemical), which has an azlactone functionality reactive with nucleophiles. Still other suitable solid supports are those fabricated of polymeric materials and having covalently, tightly associated, or incorporated sites which bind specific amino acid sequences. The general principles of affinity chromatography and solid supports for practicing affinity chromatography in which one or more specific binding partners is made available on a chromatographic bed so that binding ligands may be immobilized for the purposes of purifying the ligand are discussed in *Affinity Chromatography, Principles and Methods*, Pharmacia Publication 18-1022–29, incorporated herein by reference.

In preferred embodiments in which protecting agents are immobilized on solid supports, the step of protecting sites on the protein can be accomplished by bringing a solution containing the protein for polyethylene glycol conjugation in contact with the solid support having the immobilized protecting agent to provide a protected protein in the form of a protecting agent and protein complex. Those skilled in the art will appreciate that optimum reaction conditions depend upon the protein, the solid support and the protecting agent. Accordingly, reaction pH, reaction temperature, reaction time, and reaction medium may be varied in accordance with known principals for preparing the selected protecting agent and protein complex. The solid support having immobilized protecting agent may be contained within a column, in which case contacting the protein can involve passing the solution containing the protein through the column at a rate and under temperature and pH conditions which promote the protecting reaction.

Included within the scope of the present invention are processes in which the protecting step is carried out in solution and the protecting agent is not immobilized. Such solution based processes involve providing a solution of protecting agent and a selected protein in suitable relative amounts and under reaction conditions sufficient to cause the protecting agent and protein to form a complex. As mentioned above, reaction pH, reaction temperature, reaction time and reaction medium may be varied in accordance with known principles for binding the protecting agent and protein. Preferably, following the protecting reaction, the complex of protecting agent and protein is separated from the reaction mixture by conventional separation techniques. Suitable separation techniques include chromatographic methods such as reverse phase chromatography, normal phase chromatography, affinity chromatography, ion exchange chromatography; preparative electrophoretic methods; and selective precipitation techniques. Alternatively, the complex of protecting agent and protein is not recovered from the protecting reaction solution prior to forming the polyethylene glycol conjugated protein. In this embodiment, reactions for forming polyethylene glycol conjugated protein are carried out in the solution used for protecting the protein. Following the conjugation reactions as described below, the polyethylene glycol conjugated protein may be deprotected as described below so that the active site or sites is free and then recovered from the solution. Alternatively, the polyethylene glycol conjugated protein complexed with the protecting agent may be recovered followed by deprotecting the polyethylene glycol conjugated protein in the conjugation reaction solution and recovering the conjugated protein using any protein purification scheme including but not limited to those described above.

Reagents and procedures for forming polyethylene glycol conjugates with proteins are known in the art per se and are generally applicable to the practice of the present invention. Typically, these procedures involve first providing an activated polyethylene glycol in which one or both hydroxyl groups on a polyethylene glycol are activated, and reacting the activated polyethylene glycol with active sites on a protein selected for polyethylene glycol conjugation. The most widely utilized procedures for conjugating a protein with polyethylene glycol are based upon a nucleophilic reaction between protein amino sites (the ε-amino nitrogen of lysine or the amino terminal amine) and an activated hydroxyl of polyethylene glycol. Since sulfhydryls are also nucleophiles, cysteine sulfhydryls that are not part of a disulfide bridge are also potential reaction sites on the protein. The general principles of polyethylene glycol conjugation with proteins, and common activating reagents are described by Delgado et al. in The Uses and Properties of PEG-Linked Proteins, from *Critical Reviews in Therapeutic Drug Carrier Systems*, 9(3,4):249–304 (1992) which is incorporated herein by reference. Activated forms of polyethylene glycol and monomethoxypolyethylene glycol are commercially available and may be used in processes of the present invention. Most notably, Shearwater Polymers, Inc of Huntsville, Ala. provides a number of polyethylene glycol polymers and polyethylene glycol derivatives. The Shearwater Polymers, Inc Catalog (Shearwater Polymers, Inc. Catalog Functionalized Biocompatible Polymers for Research, 1994 incorporated herein by reference) includes a wide variety of activated polyethylene glycols suitable for coupling with proteins under a wide range of reaction conditions. This catalog additionally provides preferred reaction conditions for their derivatized polyethylene glycol reagents. Those skilled in the art having been made aware of the numerous reagents suitable for conjugating proteins with polyethylene glycol will appreciate the variety of reagent choices in view of the nature of the protein selected, the nature of the reactive amino groups or sulfhydryl groups on the protein and the end use of the conjugated protein. For example, to provide conjugated proteins having improved solubility, activity characteristics and delivery properties but not necessarily increased clinical clearance time, a succinimidyl succinate activated polyethylene glycol (SS-PEG) can be used in the conjugation reaction. The ester link to the protein is less stable and will hydrolyze in vivo, releasing the polyethylene glycol from the protein. Activated polyethylene glycols are available which will more preferentially react with amino groups as opposed to sulfhydryl groups and vice versa. Commonly selected activated polyethylene glycols include succinimidyl carbonate activated polyethylene glycols and succimidyl propionic acid polyethylene glycols.

As an alternative to selecting commercially available activated polyethylene glycols, a polyethylene glycol of interest may be activated using reagents which react with hydroxyl functionalities to form a site reactive with a site on a protein of interest. Typically, the protein reactive site is an amino group but can be a sulfhydryl or hydroxyl and the activated polyethylene glycol typically is an active ester or imidizole (See pgs 274–285 ibid.) Preferably, only one hydroxyl functionality of the polyethylene glycol is activated which can be accomplished by utilizing a monomethoxypolyethylene glycol in an activating reaction. However, processes in which two hydroxyls are activated are within the scope of the present invention. Depending upon the nature of the activating group and the nucleophilic attack, the activating moiety may or may not become incorporated into the protein following the nucleophilic reaction.

The polyethylene glycol may be of any molecular weight but is preferably in the range of about 500 to about 100,000 and more preferably in the range of 2,000 to 20,000. The criteria for selecting a specific polyethylene glycol molecular weight include, but arc not limited to, the molecular weight of the protein selected for modification, the charge on the protein, type of protein and the number and location of potential sites for conjugation. Immunological and plasma half-life characteristic of proteins conjugated with different molecular polyethylene glycols molecular weight are discussed in Delgado et al, *Critical Reviews in Therapeutic Drug Carrier Systems*, 9:249, 1992. As known in the art, in general, the greater the amount of polyethylene glycol conjugated to the protein, the longer the plasma half-life and the greater the protein solubility. Since the molecular weight cut-off for glomerular filtration is roughly 70 kDa, proteins having molecular weights less than about 70 kDa will experience lengthened plasma half-life. For proteins larger than 70 kDa, the effects of the polyethylene glycol and its molecular weight will vary with its clearance mechanism.

In general, using a polyethylene glycol having a high molecular weight in the processes of the present invention results in conjugated proteins having more polyethylene glycol per molecule of protein than using polyethylene glycol having a lower molecular weight. Thus, when a high amount of polyethylene glycol per protein molecule is desirable, the molecular weight of the polyethylene glycol is preferably up to 20,000. However, smaller molecular weight polyethylene glycols, because of their greater solution mobility, may conjugate to more sites on the protein than a higher molecular protein. Thus, when a protein has a number of desired conjugation sites it may be preferable to use a polyethylene glycol having a lower molecular weight to assure that an optimum number of sites is conjugated. This may be a particularly desirable approach when the potential conjugation sites or reaction site on the protein are in close proximity to each other. Another consideration used in selecting a polyethylene glycol molecular weight is that even though proteins treated in accordance with the present invention have protected sites, larger molecular weight polyethylene glycols may be so large that, once conjugated, their molecular size causes them to extend their spacial or steric influence so that binding or receptor sites have reduced accessibility. It is within the knowledge of those skilled in the art to determine an optimum polyethylene glycol molecular weight for any selected protein and benefits desired from the polyethylene glycol conjugation.

Subsequent to conjugating the protected protein with polyethylene glycol, the present invention further includes deprotecting the protein with a deprotecting agent. As used herein a deprotecting agent is any molecule, solution or gas having a predetermined pH, solution having a predetermined ionic strength which releases or cleaves the reversibly bound protein from the complex of protein and protecting agent. In preferred embodiments in which the protecting agent is immobilized to a solid support, deprotecting the conjugated protein can be accomplished by contacting the solid support having the immobilized protecting agent and conjugated protein with a suitable deprotecting agent. Advantageously, this technique can result in the protecting agent remaining immobilized to the solid support and available for re-use in subsequent polyethylene glycol conjugation reactions using the same solid support and immobilized protecting agent. The selected deprotecting agent and its use may vary with the nature of the complex of protecting agent and conjugated protein. More particularly, in selecting a deprotecting agent and the procedure in which it is used, the strength of the complex or the dissociation constant (Kd) for the complex of protecting agent and conjugated protein may be a consideration. For example, in many processes of the present invention, a suitable deprotecting agent may be a buffer solution having a pH which causes the protecting agent to release the conjugated protein from the protecting agent. When the complex of protecting agent and conjugated protein is strongly associated and harsh pH conditions are required to dissociate the. complex, it is typically advisable to elute the deprotected conjugated protein into a buffer system having an adjusted pH which leaves the final pH of the deprotected conjugated protein solution close to neutral.

Alternatively, deprotecting agents may be solutions having an ionic strength sufficient to disrupt the complex of protecting agent and conjugated protein and release the conjugated protein from the protecting agent. Conjugated proteins can be released from complexes of proteins and protecting agent using a more strongly binding competitive protecting agent. Additional deprotecting agents include denaturants such as urea, chelating agents such as EGTA and EDTA or other reagents including potassium isothiocyanate and chaotropic salts. The characteristics of many ligand-:binding partner complexes and suitable reagents for deprotecting the complex are discussed in Pharmacia *Affinity Chromatography Principles and Methods*, 18-1022–29 pg 117–119 (1993). In any case, the deprotecting agent is selected such that it causes the protein to have a greater affinity for the solution containing the deprotecting agent than the protein has for the protecting agent. For example, when the protein selected for modification is TNFR and the protecting agent is a TNFR neutralizing antibody, a suitable deprotecting agent is a low pH buffer solution because TNFR dissociates from its neutralizing antibody at low pH's.

In embodiments in which the solid support is configured in a column, deprotecting the conjugated protein is conveniently carried out by passing a solution of the deprotecting agent through the column under conditions which allow the deprotecting agent to deprotect the protein. The polyethylene glycol conjugated protein can be collected and recovered directly from the solution of deprotecting agent. When the solid support is contained within a container, the solid support having the immobilized protecting agent can be separated from the solution containing deprotected polyethylene glycol conjugated protein by filtering, centrifuging, or other separation techniques known in the art.

When the complex of protecting agent and polyethylene glycol conjugated protein is in solution, or not immobilized to a solid support, the conjugated protein can be deprotected by adding deprotecting agent to the conjugated protein solution. Criteria for selecting deprotecting agents are the same as those described above and may be buffer solutions having a selected pH, solutions having a selected ionic strength, or other solutions or possibly gases having properties suitable for deprotecting proteins from a binding partner. The conditions for the deprotecting step should be such that sufficient time and temperature are maintained to allow the deprotecting agent to cause the conjugated protein to dissociate from the protecting agent. The deprotected polyethylene glycol conjugated protein can be recovered from the solution of protecting agent using standard protein recovery and purification techniques including preparative liquid chromatography, ion exchange chromatography and preparative electrophoretic techniques.

While the above described polyethylene glycol conjugation procedures are those in which the result is polyethylene glycol conjugated to protein via a covalent bond, it is within the scope of the present invention to include procedures in which the conjugation is via a different association. In the context of the present invention, proteins may be modified by conjugating them to polyethylene glycol using a variety of different linking or conjugating mechanisms. For example, a protein selected for conjugation can be derivatized at an amino group or other suitably reactive functionality with a poly A oligonucleotide and then conjugated with a polyethylene glycol derivatized with a poly T oligonucleotide. Another approach involves derivatizing the protein with a functionality having a known specific binding partner and then conjugating the protein with polyethylene glycol which has been derivatized with the binding partner for the functionality. For example, a protein can be derivatized with biotin and the polyethylene glycol derivatized with strepavidin or avidin (or vice versa). This results in the specific binding of polyethylene glycol to those protein sites having the biotin. A number of reagents for modifying proteins for the purpose of introducing certain functionalities are commercially available. For example, the Pierce ImmunoTechnology catalogue identifies and provides access to a variety of reagents associated with protein modification. Among these are Traut's Reagents and SATA (Pierce ImmunoTechnology Catalogue, Vol I, pg E-14) which can introduce active groups at N-terminal amines and lysine amino functionalities. These active groups provide sites for further introducing functionalities for reacting more specifically with polyethylene glycol. Those skilled in the art will also recognize that ionic interactions between polyethylene glycol and a protein of interest are also possible. For example, an association between an ionic moiety on the protein and its counter ion on polyethylene glycol can be utilized if the association is sufficiently strong to remain associated under physiological conditions.

Further embodiments of the present invention which may utilize prior modified proteins include those processes in which the protein selected for conjugation has too few potential polyethylene glycol conjugation sites or no potential polyethylene glycol conjugation sites outside the protected amino acid region. By modifying the selected protein to introduce amino and sulfhydryl sites on the protein sufficient polyethylene glycol may be conjugated to the selected protein to provide the desired benefits. Modifying the selected protein can be achieved using genetic engineering methodologies or chemical modification. As mentioned above, processes and reagents for modifying proteins to achieve a large variety of desired results are well known in the art. In particular, in Wong, *Chemistry of Protein Conjugation and Cross-linking*, CRC Press, 1993, incorporated herein by reference, provides information relating to conjugation reagents and process conditions.

While polyethylene glycol is a preferred protein conjugating reactant, a variety of additional polymer modifiers have been used to modify proteins. These include modified polyethylene glycols, branched polyethylene glycols, crosslinked polyethylene glycols, dextrans, polyvinylpyrrolidone, polyvinylalcohol, polyamino acids, albumin and gelatins. Those skilled in the art will appreciate, once having an understanding of the present invention, that the principles and methods described herein can be applied to processes for modifying proteins with any of these additional reagents.

Proteins modified according to the procedures described herein have benefits associated with polyethylene glycol conjugation without the expected significant loss in activity. By merely applying known testing procedures to establish post conjugation activity, the benefits to proteins conjugated in accordance with the present invention can be demonstrated. Activity tests are specific for the protein and should be selected according to the protein of interest. Many proteins have more than one site associated with one or activities The selection of activity measurement for such proteins depends upon the activity of interest and the site which is specifically protected for the conjugation reaction. In addition to evaluating polyethylene glycol conjugated proteins for their activity, they can be analyzed for the degree of polyethylene glycol substitution, molecular weight, and sites of conjugation. Techniques for performing these analytical procedures are well known and some are described with respect to polyethylene glycol conjugated proteins in *Critical Reviews in Therapeutic Drug Carrier Systems*, 9(3:4):285–291, 1992. Example 3 below describe procedures for determining molecular weight or hydrodynamic volumes, degree of polyethylene glycol substitution, and bioactivity of p75 TNFR:Fc fusion protein conjugated in accordance with the present invention. Characterizing conjugated proteins for their molecular weight and degree of substitution is not necessary for the practice of the present invention but does provide insight into the specifics of the conjugation product.

The following examples are presented in order to provide a more detailed description of specific embodiments of the present invention and are not to be construed as limiting the scope of the invention.

EXAMPLE 1

Site Protected TNFR:Fc Conjugation

The following describes a process for the polyethylene glycol conjugation of a dimeric TNF receptor in accordance with the present invention. The selected protein was a covalently dimerized fusion construct of two extracellular, ligand binding portions of the human p75 TNF receptor fused together by an IgG1Fc moiety (TNFR:Fc) (Mohler et al. *J Immunol.* 151:1548–1561, 1993) TNFR:Fc is a 120 kDa protein which binds to TNFα and LTα with high affinity.

Recombinant TNFR:Fc was obtained by expressing the protein in CHO cells using the dihydrofolate reductase selectable amplifiable marker. Suspension cells were centrifuged and resuspended into serum-free medium in a controlled bioreactor. The product was collected after 7 days and the TNFR:Fc molecule was purified using protein A affinity chromatography followed by an ion-exchange chromatography step.

An antihuman TNFR:Fc neutralizing monoclonal antibody (hu TNFR M1) was generated as described in Ware et al. *Immunol.* 147:4229. Nineteen milligrams (19 mg) of the hu TNFR M1 was dialyzed into 1 L of coupling buffer of 0.5 M sodium citrate and 0.1 M sodium bicarbonate adjusted to pH 8.6 with 1 M NaOH. After overnight dialysis the dialyzing buffer was replaced with a second 1 L volume and dialysis continued for one day. An affinity column was prepared by loading 0.37 g of 3M EMPHAZE™ Biosupport Medium (purchased from 3M of Minneapolis, Minn.) into a 3 mL Amicon column. The 3M EMPHAZE Biosupport Medium is fabricated of hydrophilic highly crosslinked bis-acrylamide/azlactone copolymeric beads having azlactone functionalities which covalently attach biomolecules through their nucleophilic functionalities.

Human TNFR M1 was immobilized to the EMPHAZE™ solid support by adding 5 mL of dialyzed huTNFR M1 solution having a total-huTNFR M1 content of 17 mgs to the beads following the manufacturer's instructions for reacting proteins with the azlactone functionalities. After the reaction, the beads and solution were centrifuged until a bead pellet formed in the centrifuge tube. The supernatant was decanted off and the beads were quenched with 10 volumes of 3.0 M ethanolamine at pH 9 to block unreacted azlactone sites on the beads. After quenching for 2.5 hours per manufacturer's instructions, the beads were centrifuged to a pellet and the ethanolamine supernatant decanted from the pellet. Then 25 mL of protein free PBS was added to the beads and the mixture was vortexed for 10 minutes. Following the vortex mixing, the PBS was removed and an additional 25 mL of PBS was added to the mixture.

After immobilizing the antibody on the solid support, the beads having immobilized antibody were transferred to an Amicon column. Then active sites on TNFR:Fc were protected with the M1 antibody protecting agent by passing a solution containing 0.5 mg of TNFR:Fc over the beads at a flow rate of 0.1 mL/min. After the protecting reaction was complete, the protected TNFR:Fc was conjugated with a 5,000 MW polyethylene glycol by continually passing a solution of 10 mg SC-PEG-5000 (5,000 MW succinimidyl carbonate activated monomethoxypolyethylene glycol purchased from Shearwater Polymers, Birmingham, Ala.) in 5 mL of 50 mM $Na_2HPO_4$ pH 8.5 through the EMPHAZE™ column at 1 mL/min overnight at 25° C.

Following the conjugation reaction the polyethylene glycol conjugated TNFR:Fc was deprotected by passing a 50 mM solution of sodium citrate adjusted to pH 3.0 through the column at a flow rate of 1 mL/min for 60 minutes. Then the solution of recovered polyethylene glycol conjugated TNFR:Fc was neutralized to pH 7.4 with 0.1 N NaOH.

EXAMPLE 2

Control TNFR:Fc Conjugation

The following describes a process for preparing a control polyethylene glycol conjugated TNFR:Fc in a procedure which does not include a step for protecting the TNFR:Fc. One hundred micrograms (100 μg) of recombinant human (rhu)TNFR:Fc utilized in Example 1 in 400 μL of 50 mM $Na_2HPO_4$ at pH 8.5, was allowed to react with SC-PEG 5000 at different molar ratios of polyethylene glycol to protein (calculated as number of lysine residues in TNFR:Fc) overnight at 4° C. The molar ratios of protein to lysine residues were 1.25:1, 0.625:2, 0.313:1, 0.156:1, and 0.078:1. The polyethylene glycol conjugated TNFR:Fc was purified by size exclusion chromatography using a Bio-Sil 400 column available from BioRad, Hercules, Calif. according to manufacturer's directions for protein purification.

EXAMPLE 3

Characterization of Conjugated TNFR:FC

The following describes the characterization of conjugated protected TNFR:Fc prepared in Example 1 and the control TNFR:Fc prepared in Example 2. The characterization included analyzing the conjugated proteins for number of polyethylene glycol chains per TNFR:Fc molecule (degree of conjugation), protein molecular weight, and conjugated protein bioactivity. Additionally, nonconjugated TNFR:Fc control samples were analyzed using the same analytical methods.

Degree of Polyethylene Glycol Conjugation

The concentration of the proteins in the solutions obtained in Example 1 and Example 2 was determined using a Beckman Amino Acid Analyzer according to manufacturer's instruction. Then the number of polyethylene glycol units per molecule of TNFR:Fc in solution was determined using the Fluorescamine method generally described in Sartore et al. *Applied Biochemistry and Biotechnology*, 31:213, 1991. The referenced Fluorescamine method involves using the fluorescamine reagent, a nonfluorescing reagent which reacts with primary amines to produce a highly fluorescing quantitatively detectable product. In particular, the volume of each of the protein solutions was adjusted so that the concentration of protein was about 200 μg/mL. Then, each protein solution was added to a series of 5 tubes such that the tubes had the following volumes: 0.5 mL, 0.4 mL, 0.3 mL, 0.2 mL and 0.1 mL. Each tube was diluted to a total volume of 2.0 mL with 0.1 M sodium phosphate buffer at pH 8.0.

Sequentially, 1.0 mL of a solution of 0.3 mg/mL fluorescamine (purchased from Sigma Chemical Company, St. Louis, Mo.) in acetone was added to each of the sample tubes and a control tube containing 2 mL of buffer solution. After vigorous mixing for 5 minutes each sample was analyzed in a fluorescence spectrometer at an excitation wavelength of 390 nm and an emission wavelength of 475 nm. To determine the relative amount of lysine modification a plot of fluorescence units vs protein concentration was prepared. The percentage of polyethylene glycol conjugation was determined as 1-(slope modified protein/slope unmodified protein)×100.

Molecular Size Analysis

The relative molecular size of the unprotected conjugated TNFR:Fc samples, the protected conjugated TNFR:Fc sample, and the control TNFR:Fc sample were determined using standard size exclusion procedures and a Bio-Sil SEC 400 column. The molecular size was determined using high molecular weight protein standards and more accurately reflects a hydrodynamic volume or relative size of the conjugated proteins as opposed to an accurate molecular weight. This is because the standards are proteins having known molecular weights and not polyethylene glycol modified proteins. Polyethylene glycol chains are extended in solution and have larger radii than proteins. Thus, conjugating polyethylene glycol to proteins increases their apparent molecular weight because the conjugated proteins have higher hydrodynamic volumes per actual molecular weight increase attributed to the polyethylene glycol. The effect is a greater relative molecular size when compared with protein standards.

Bioactivity of Conjugated TNFR:Fc and Unconjugated TNFR:Fc

The bioactivities of the polyethylene glycol conjugated TNFR:Fc prepared in Example 1 and Example 2 and an unconjugated TNFR:Fc were determined using a bioassay generally described in Onozaki et al. *J. Immunology*135:3962 (1985) and Nakai et al. *Biochem. Biophys. Res. Comm.* 154:1189 (1988). The bioassay is based upon the inhibitory response of the A375 human malignant melanoma adherent cell line to TNFα. Soluble TNFR:Fc can specifically neutralize the inhibitory activity of TNFα in a dose dependent manner. To perform the bioassay, 375 cell line (ATCC CRL 1872) was harvested using a trypsin-EDTA solution to remove the cell monolayer from flasks. The harvested cells were washed with an assay medium of Dulbeccos' Modified Eagles Medium with added fetal bovine serum, non-essential amino acids, and sodium pyruvate (all purchased from GIBCO).

Ninety-six well plates were prepared with serial dilutions of working solutions of unmodified TNFR:Fc prepared as described in Example 1, blocked TNFR:Fc conjugated with polyethylene glycol as described in Example 1, and unprotected TNFR:Fc conjugated with polyethylene glycol prepared as described in Example 2. Then, equal amounts of TNFAα (R & D Systems, Cat. No. #210-CA TF) in the assay medium described above were added to wells in 96 well plates followed by adding an equal volume of about $4 \times 10^5$ harvested cell suspension to each well.

The plates were placed in a humidity chamber at 37° C. and 10% $CO_2$ and the cells were allowed to incubate for 72 hours. Then the plates were removed from the chamber and the cells were washed with PBS solution, blotted, and fixed with ethyl alcohol. Viable cells were made visible by staining the fixed cells with 0.1% aqueous crystal violet solution. After washing the plates with water and blotting the cells, 2% sodium deoxycholate solution was added to each well and the wells of each plate were read for optical density at 570 nm on a plate reader using Delta Soft microplate analysis software. Standard bioactivity units were assigned for each sample and adjusted to take into account the concentration of TNFR:Fc in the wells. Wells containing blanks were assigned a bioactivity of zero and those containing unmodified or unconjugated TNFR:Fc were assigned a bioactivity of 100.

Table II presents the results of the degree of polyethylene glycol conjugation analyses, the molecular size analyses, and the bioactivity tests for each of the TNFR:Fc proteins studies.

TABLE II

Results of Conjugated TNFR:Fc Characterization

| Sample | Degree of PEG Subst. [5] | Mol Size [3] | % Bio-activity [4] |
|---|---|---|---|
| Unprotected TNFR:Fc [1] | | | |
| 0:1 | 0 | 370,960 | 100 |
| 0.078:1 | 1.8 | 494,937 | 74 |
| 0.156:1 | 3.2 | 648,335 | 60 |
| 0.313:1 | 4.7 | 865,013 | 38 |
| 0.625:1 | 4.5 | 1,092.262 | 10 |
| 1.25:1 | ND [2] | 1,174,221 | 0 |
| Protected TNFR:Fc | | | |
| #1 | 6.5 | 833,829 | 131 |
| #2 | 5.4 | ND | 124 |
| #3 | 5.2 | ND | 110 |
| #4 | ND | ND | 120 |

[1] Ratios are moles of activated PEG:moles TNFR:Fc lysine residues
[2] Not Determined
[3] Relative molecular size; measures hydrodynamic volume
[4] Relative bioactivity; unconjugated TNFR:Fc assigned 100
[5] Number of polyethylene glycol units per TNFR:Fc molecule As demonstrated by the results of the characterization analyses shown in Table II, proteins which were protected prior to their conjugation do not show a decrease in their activity. In fact, in the case of TNFR:Fc, the protein's bioactivity is enhanced. When a TNFR:Fc is not protected prior to its conjugation with polyethylene glycol, it shows an increase in the number of polyethylene glycol units or chains per TNFR:Fc molecule up to about 4.5 units polyethylene glycol per TNFR:Fc molecule. Similarly, and as expected, the relative molecular weight of the conjugated protein increases with increasing amount of polyethylene glycol in the reaction mixture. Also, as expected, the activity of TNFR:Fc conjugated without the benefit of a blocked site decreases with increasing ratios of polyethylene glycol:lysine residues in the conjugation reaction. Surprisingly, when a protein is protected prior to the conjugation reaction, the activity of the conjugated protein is measured at an even higher activity than that of the unconjugated control protein. The activity of the protein which was conjugated under protected conditions is enhanced notwithstanding the relatively high number of polyethylene glycol units conjugated to the protein. That is, under the reaction conditions, between approximately 5 to 6 polyethylene glycol units per TNFR:Fc conjugate to the protected protein resulting in bioactivity which are measured at from 110% to 130% of the control protein. By contrast, when an average of about 4.5 polyethylene glycol units conjugate to an unprotected TNFR:Fc the activity drops to less than 40% of that of a control unconjugated protein. Clearly, processes of the present invention provide polyethylene glycol conjugated proteins having enhanced benefits over prior art methods.

EXAMPLE 4

Generating TNFR:Fc Peptide Maps

In order to study the sites of polyethylene glycol conjugation and the activity associated with the conjugation site, peptide maps were generated for conjugation products of unprotected TNFR:Fc, the products conjugated in accordance with the present invention, and unconjugated control TNFR:Fc. The peptide maps were generated by digesting the TNFR:Fc with trypsin, an enzyme which acts on lysyl and arginyl bonds of peptide chains. Native non-glycosylated TNFR:Fc treated with trypsin is expected to form 39 fragments since there are 38 sites having an lysine or arginine residue. Polyethylene glycol is known to conjugate through available amino functionalities on lysine and the reactivity of trypsin toward a conjugated lysine site is altered. Accordingly, it is expected that the trypsin digestion map of a conjugated protein compared with a non conjugated protein will provide information relating to conjugation sites and the degree of conjugation.

The trypsin digestion was accomplished by diluting 200 μL of about 10 mg/mL protein solution with 500 μL of 7M guanidine:HCl, and 0.1 M TRIS-HCl, at pH 8.3. Then 7 μL of 1M dithiothreitol was added to the protein solution and the solution was incubated at 65° C. for 15 minutes to reduce the protein. After cooling the reduced protein solution 15.4 μL of 1M aqueous iodoacetamide was added and the reduced protein solution was incubated at room temperature for 10 minutes. After adding another 15.4 μL of 1M dithiothreitol to the solution, it was incubated for 10 minutes and diluted to a final volume of 7 mL by adding 6.276 mL of 0.1 M TRIS, at pH 7.5. A solution of N-glycanase was added to the protein solution to a final ratio of 2 U N-glycanase/100 μg TNFR:Fc. This solution was incubated for 1 hour at 37° C. Then, sufficient trypsin solution containing 1 μg/μL trypsin was added to the protein solution to make a final trypsin:wt protein ratio of 1:10. The sample was allowed to digest by incubating it for 5 hours at 37° C. Following the incubation, the digestion was quenched by boiling the digest for 3 minutes and adjusting the digest to pH 2 using 10% trifluoroacetic acid.

The above procedure was performed using samples of unconjugated TNFR:Fc, TNFR:Fc conjugated subsequent to protecting its binding site, and TNFR:Fc conjugated without blocking its binding site. All samples were then chromatographed using a Waters HPLC system equipped with a Kromasil C18, 5 μ, 100 A pore size, 3.2×250 mm with a guard column. A gradient mobile phase was used with solvent A containing aqueous 0.15% TFA and solvent B containing 0.12% TFA in 80% $CH_3CN$. The flow rate was 0.5 mL/min with a run time of 215 minutes. A uv detector monitored absorbances at 220 nm and at 280 nm.

Figure 2:
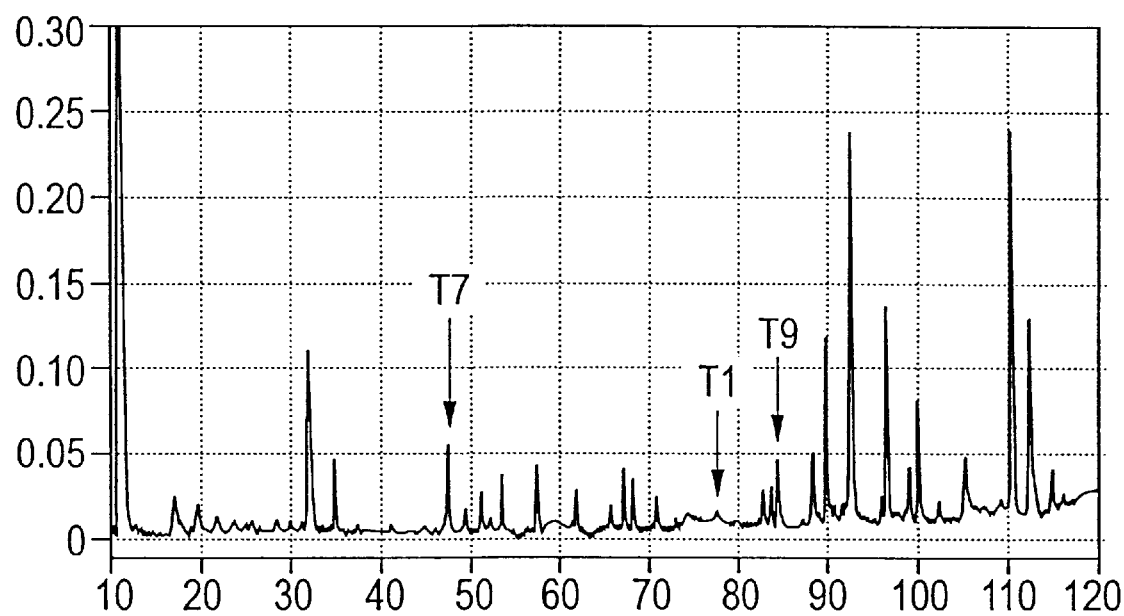
FIG. 2 is a conjugated p75 TNFR:FC peptide map obtained by the reverse phase HPLC separation of polyethylene glycol conjugated unprotected TNFR:Fc trypsin digestion fragments.
Figure 3:
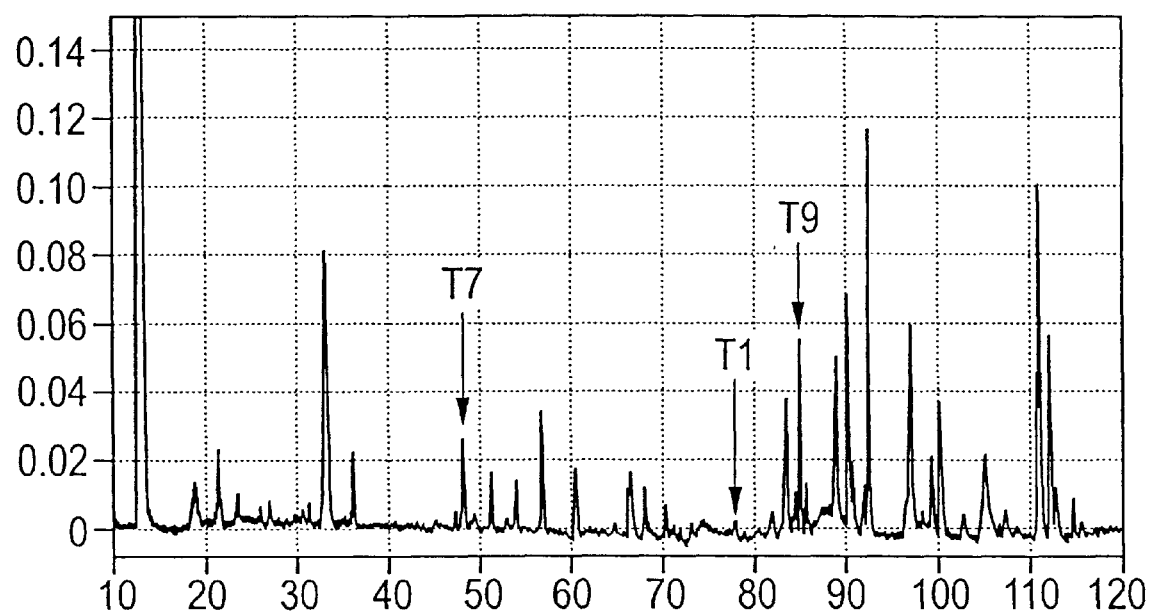
FIG. 3 is a conjugated p75 TNFR:Fc peptide map obtained by the reverse phase HPLC: separation of polyethylene glycol conjugated protected TNFR:Fc trypsin digestion fragments.

The tryptic peptide map chromatograms obtained for the control unconjugated TNFR:Fc, TNFR:Fc conjugated without the protecting step, and TNFR:Fc conjugated subsequent to a protection step are presented in FIG. 1, FIG. 2, and FIG. 3, respectively. In general, the maps demonstrate that conjugating protected TNFR:Fc and unprotected TNFR:Fc results in the disappearance of peaks from the map or a reduction in peak height. In particular, note the peaks identified as T7, T1 and T9. The T7 peak is confirmed to be a trypsin digestion fragment which is flanked by arginine on both ends. Since neither of the active sites for this digestion fragment contains a lysine, this fragment is not expected to be affected by a polyethylene glycol conjugation reaction. Accordingly, the peak is expected to be the same for a TNFR:Fc digestion sample regardless of whether or not the TNFR:Fc had undergone a polyethylene glycol conjugation reaction. For this reason, the T7 peak was used to normalize all other peaks of the three chromatograms and is presented as having equal peak heights in the three maps.

The T1 fragment has been identified as the N terminus of TNFR:Fc and is very apparent in the trypsin digestion map of the unconjugated control protein (FIG. 1) but absent in the maps of the protein conjugate without prior protection (FIG. 2) and the map of the protein conjugated subsequent to a protecting step. This is expected since the N-terminus contains a very reactive amino functionality which will quickly conjugate with an activated polyethylene glycol functionality. The digested polyethylene glycol conjugated fragment will not elute at the same elution volume during the HPLC separation.

Interestingly, the peak identified as T9 is known to correspond to a fragment that includes amino acid residue lys108 which is believed to be involved with binding TNFα. Significantly, T9 peak is substantially reduced in the map associated with the digestion of TNFR:Fc conjugated without prior protecting (FIG. 2) demonstrating that this lysine residue was not an active site for trypsin digestion, probably as a consequence of the unprotected polyethylene glycol conjugation reaction. In contrast, the T9 peak associated with the digestion map of TNFR:Fc conjugated subsequent to protection (FIG. 3) is not diminished in size demonstrating that the lysine residue was not effected by the conjugation reaction and remains active during trypsin digestion. This data provides a strong suggestion that a TNFR:Fc was sufficiently protected prior to the conjugation reaction and explains the retained activity associated with the TNFR:Fc conjugated in accordance with the present invention.

EXAMPLE 5

Conjugating IL-4R

The following describes conjugating IL-4 receptor (IL-4R) utilizing a site protected methodology. Recombinant IL-4R produced in CHO cells was the selected protein and the protecting agent used was IL-4R monoclonal antibody, which neutralizes the activity of IL-4R. Methods for expressing IL-4R in CHO cells and preparing a neutralizing antibody are described in PCT Publication WO 90/05183. The TL-4R neutralizing antibody was immobilized to 3M EMPHAZE™ Biosupport Medium in substantially the same manner as that described in Example 1 using 15 mg of neutralizing antibody and 0.25 g of 3M EMPHAZE™.

The beads having immobilized antibody were transferred to a 2 mL stainless steel Amicon column (VL 11×25) and packed by flowing PBS through the column at 1 mL/min for 2 minutes. The column was equilibrated by flowing 50 mM $Na_2HPO_4$ (pH 8.5) for 20 minutes at 0.5 mL/min. Then, 400 μl of IL-4R solution (5.0 mg/mL IL-4R in 20 mM Tris, pH 7.4) was loaded onto the column in 50 mM $Na_2HPO_4$ (pH 8.5). The resulting solution was continuously passed through the column at 0.5 mL/min for 1 hour.

After the protecting reaction, the IL-4R was conjugated with polyethylene glycol by adding 50 mg of succinimidyl propionic acid (SPA) activated PEG5000 (a 10 fold molar excess polyethylene glycol to lysine residues on the WL-4R) in 6 mL of 50 mM $Na_2HPO_4$ (pH 8.5) by pumping the solution into the resin in the column. The polyethylene glycol conjugation reaction was allowed to proceed overnight. Unbound polyethylene glycol and conjugation reaction byproducts were rinsed from the column by pumping 50 mM $Na_2HPO_4$ (pH 8.5) for 60 minutes at 0.5 mL/min.

The conjugated IL-4R was deprotected eluted from the column by pumping 0.2M sodium citrate, (pH 2.5) at 0.5 mL per minute for 1 hour through the column. Fractions of eluted material were collected and analyzed by UV absorbance at 280 nm. Samples containing protein were neutralized to pH 7.0 by the addition of 0.1 N NaOH.

The conjugated IL-4R was characterized by SDS-PAGE and size exclusion chromatography analysis. Each of these techniques confirmed that protected IL-4R conjugated with polyethylene glycol.

EXAMPLE 6

Conjugating huGM-CSF

Recombinant huGM-CSF was produced in yeast as described in Gillis, D. L. ct al *Behring Inst. Mitt.*, 83: 1–7

(1988). Eighty-nine milligrams of GM-CSF monoclonal antibody, Immunex designation M8, specific for the N-terminus of huGM-CSF was conjugated to 25 mL of cyanogen bromide activated Sepharose according to the manufacturers instructions.

After the antibody was immobilized to the resin, it was poured into a 50 mL Amicon column and packed by flowing PBS through the column. GM-CSF (1.5 mL at 6.8 mg/mL $NaH_2PO_4$, (pH 7.0) was loaded onto the column in 50 mM $NaH_2PO_4$ (pH 7.0) and the solution was continuously passed through the column at 0.5 mL/min for 2 hours. Then the column was equilibrated by passing 50 mM $NaH_2PO_4$ (pH 8.5) through the column for 1 hour.

The GM-CSF was conjugated with polyethylene glycol by adding 500 mg of succinimidyl carbonate (SC) activated polyethylene lycol 5000 (a 50 fold molar excess of polyethylene glycol to residual lysine amino groups on GM-CSF) in 10 mL of 50 mM $NaH_2PO_4$ (pH 8.5) and pumping the solution through the column at 0.1 mL/min overnight.

Conjugated GM-CSF was eluted from the column by pumping 50 mM $NaH_2PO_4$ (pH 11.0) at 1 mL/min for 1 hour. Fractions of eluted material were collected and analyzed by UV absorbance at 280 nm. Samples containing protein were neutralized to pH 7.1 by the addition of 1 M HCl. The conjugated GM-CSF was characterized by SDS-PAGE and MALDI-TOF mass spectrometry. Each of these techniques confirmed that GM-CSF had been conjugated with PEG. The change in mass was from approximately 14 kDa, the molecular weight of unmodified GM-CSF, to 29 kDa. The detected molecular weight change indicates that three molecules of 5,000 molecular weight polyethylene glycol conjugated to each molecule of GM-CSF.

What is claimed is:

1. A process for conjugating p75 TNFR:Fc with polyethylene glycol, said process comprising the steps of:
    a) binding TNFR:Fc neutralizing antibody to the p75 TNFR:Fc to provide a site protected p75 TNFR:Fc; and
    b) contacting the site protected p75 TNFR:Fc with polyethylene glycol under conditions sufficient to conjugate the polyethylene glycol to the site protected p75 TNFR:Fc.

2. The process of claim 1 wherein the step of contacting the protected p75 TNFR:Fc with polyethylene glycol comprises causing an activated polyethylene glycol to react with nucleophiles on the p75 TNFR:Fc.

3. The process of claim 1 wherein the step of binding p75 TNFR:Fc neutralizing antibody to p75 TNFR:Fc comprises the steps of:

a) immobilizing TNFR:Fc neutralizing antibody to a solid support; and,
    b) bringing p75 TNFR:Fc in contact with the immobilized TNFR:Fc neutralizing antibody under conditions which cause TNFR:Fc neutralizing antibody to reversibly bind p75 TNFR:Fc, providing a protected p75 TNFR:Fc.

4. The process of claim 3 wherein the solid support comprises functional groups which covalently binds the TNFR:Fc neutralizing antibody.

5. The process of claim 3 further comprising the step of deprotecting the p75 TNFR:Fc.

6. The process of claim 5 wherein the step of deprotecting the protected p75 TNFR:Fc comprises treating the protected p75 TNFR:Fc with a deprotecting agent, the deprotecting agent being which dissociating the p75 TNFR:Fc from the protecting agent.

7. The process of claim 6 further comprising the step of recovering the polyethylene glycol conjugated p75 TNFR:Fc.

8. A polyethylene glycol conjugated p75 TNFR:Fc prepared according to the process of claim 1.

9. A process for modifying a p75 TNFR:Fc fusion protein, said process comprising the steps of:
    a) immobilizing a TNFR:Fc neutralizing antibody to a solid support;
    b) bringing the p75 TNFR:Fc fusion protein in contact with the immobilized TNFR:Fc neutralizing antibody under conditions which cause the TNFR:Fc receptor neutralizing antibody to bind to the p75 TNFR:Fc fusion protein; and
    c) contacting the protected p75 TNFR:Fc fusion protein with polyethylene glycol under conditions sufficient to conjugate the polyethylene glycol to the p75 TNFR:Fc fusion protein.

10. The process of claim 9 further comprising the step of deprotecting the protected and conjugated p5TNFR:Fc fusion protein.

11. The process of claim 10 wherein the step of deprotecting the protected p75 TNFR:Fc fusion protein comprises treating the protected p75 TNFR:Fc with a deprotecting agent, the deprotecting agent being capable of dissociating the p75 TNFR:Fc fusion protein from the protecting agent.

12. The process of claim 10 further comprising the step of recovering the polyethylene glycol conjugated p75 TNFR:Fc fusion protein.

13. A polyethylene glycol conjugated p75 TNFR:Fc fusion protein prepared according to the process of claim 9.

* * * * *